United States Patent
Zhang

(10) Patent No.: US 11,020,415 B2
(45) Date of Patent: Jun. 1, 2021

(54) USE OF ALBIFLORIN IN PREPARATION OF PRODUCTS FOR IMPROVING FUNCTION OF INTESTINAL FLORA SYSTEM

(71) Applicant: Zuoguang Zhang, Beijing (CN)

(72) Inventor: Zuoguang Zhang, Beijing (CN)

(*) Notice: Subject to any disclaimer, the term of this patent is extended or adjusted under 35 U.S.C. 154(b) by 4 days.

(21) Appl. No.: 16/340,470

(22) PCT Filed: Aug. 4, 2017

(86) PCT No.: PCT/CN2017/095986
§ 371 (c)(1),
(2) Date: Apr. 9, 2019

(87) PCT Pub. No.: WO2018/068566
PCT Pub. Date: Apr. 19, 2018

(65) Prior Publication Data
US 2020/0046748 A1 Feb. 13, 2020

(30) Foreign Application Priority Data

Oct. 11, 2016 (CN) .......................... 201610884497.7

(51) Int. Cl.
*A61K 31/7048* (2006.01)
*A23L 33/105* (2016.01)
*A61P 1/00* (2006.01)

(52) U.S. Cl.
CPC ........ *A61K 31/7048* (2013.01); *A23L 33/105* (2016.08); *A61P 1/00* (2018.01); *A23V 2002/00* (2013.01)

(58) Field of Classification Search
CPC ..... A61K 31/7048; A23L 33/105; A61P 1/00; A23V 2002/00
See application file for complete search history.

(56) References Cited

U.S. PATENT DOCUMENTS

2012/0270820 A1\* 10/2012 Zhang .................. A61K 9/4866
514/27

FOREIGN PATENT DOCUMENTS

| CN | 101623366 A | 1/2010 |
|---|---|---|
| CN | 101940583 A | 1/2011 |
| CN | 103179973 A | 6/2013 |
| CN | 103417561 A | 12/2013 |
| WO | 2010/133015 A1 | 11/2010 |
| WO | 2011/003226 A1 | 1/2011 |
| WO | 2011/047576 A1 | 4/2011 |
| WO | 2012/068958 A1 | 5/2012 |
| WO | 2016/134563 A1 | 9/2016 |

OTHER PUBLICATIONS

Definition of prevent, Oxford English Dictionary Online, http://dictionary.oed.com/, accessed online Mar. 27, 2010, especially definition 9a. at p. 2. (Year: 2010).\*
Lee et al., PLOS One, 2015, 10(7), e0133283, 12 pages. (Year: 2015).\*
International Search Report dated Oct. 27, 2017, issued in International Application No. PCT/CN2017/095986, filed Aug. 4, 2017, 8 pages.
Written Opinion dated Oct. 27, 2017, issued in International Application No. PCT/CN2017/095986, filed Aug. 4, 2017, 11 pages.
Search Report dated Mar. 22, 2019, issued in Chinese Application No. 2017106599091, filed Aug. 4, 2017, 4 pages.

\* cited by examiner

*Primary Examiner* — Jonathan S Lau
(74) *Attorney, Agent, or Firm* — Christensen O'Connor Johnson Kindness PLLC

(57) ABSTRACT

Use of albiflorin or a pharmaceutically acceptable salt thereof in the preparation of a product for regulating and improving the balance of human intestinal flora. Albiflorin or a pharmaceutically acceptable salt thereof, as a regulator for improving the function of intestinal flora system, can be used in the preparation of a medicament, a health care product, a food, a food additive, or a nutritional supplement that ameliorates and treats a sub-health status and/or a disease caused by intestinal flora disturbance; the sub-health status is selected from intestinal system dysfunction and/or affective disorder; and the disease is selected from one or more of irritable bowel syndrome, depression, anxiety, colitis, and colon cancer.

8 Claims, 5 Drawing Sheets

USE OF ALBIFLORIN IN PREPARATION OF PRODUCTS FOR IMPROVING FUNCTION OF INTESTINAL FLORA SYSTEM

CROSS-REFERENCES TO RELATED APPLICATIONS

This application is a National Stage of International Application No. PCT/CN2017/095986, filed Aug. 4, 2017, which claims priority to Chinese Application No. 201610884497.7, filed Oct. 11, 2016, the disclosures of which are incorporated herein by reference in their entirety.

TECHNICAL FIELD

The invention belongs to the field of medicine, relates to use of albiflorin, and more particularly to use of albiflorin in the preparation of products for improving the function of intestinal flora system and increasing the amount of intestinal probiotics, especially lactic acid bacteria, including its use in the preparation of medicaments, foods, health care products, food additives or nutritional regulators or the like for preventing and/or treating sub-health statuses and/or diseases caused by intestinal flora disturbance.

BACKGROUND ART

Intestinal micro-ecosystem is the largest and most important micro-ecosystem in a human body. The total weight of intestinal bacteria in a healthy adult can reach 1-1.5 kg. Under normal circumstances, the intestinal flora in a human body forms a symbiotic relationship with the host cells and is in a dynamic and balanced ecological environment. The role of intestinal bacteria and its impact on human health have attracted the attention of the medical industry. Intestinal flora continuously exchanges information with the host cells, evolves together with the host, regulates various metabolic pathways of the host, influences the immune-anti-inflammatory axis, and is closely related to the physiological and biochemical activities of the host, thereby affecting the health of the host. More and more studies have shown that, the disorder and dysfunction of intestinal flora composition have a close relationship with heart diseases, liver cancer, Parkinson's disease, depression, Alzheimer's disease, irritable bowel syndrome, kidney infection, obesity and diabetes, etc.

Recent studies have found that intestinal flora plays an important role in the onset of depression and anxiety. Some intestinal flora can promote the onset of depression and anxiety by interfering with the metabolism of amino acids and carbohydrates in the host organism. Treatment of mental disorders, such as depression and anxiety by regulating the ecology of intestinal flora is an important topic in the current medical research. Intestinal flora disturbance is also one of the important reasons for promoting the onset of irritable bowel syndrome, colitis and colon cancer. However, regarding the products that relieve irritable bowel syndrome, prevent and treat colitis and colon cancer by regulating intestinal flora disturbances, the current technology only stays at the level of such beverages and health care foods supplementing exogenous probiotics or lactic acid bacteria, and whether they have the function of regulating intestinal flora and the mechanism of this function are not fully understood yet.

The development of medicaments and health care products that regulate and restore the balance of intestinal flora has become an important topic in the current development of pharmaceuticals and functional foods. At the beginning of September 2016, hosted by the General Hospital of the Chinese People's Liberation Army and the China Health Promotion Foundation, a number of top three hospitals conducted a discussion on the issues on detection techniques and intervention for intestinal microorganisms in Beijing, suggesting that appropriate supplementation of dietary fiber has great importance on the construction of good intestinal flora. The Jiuyetang Probiotic Solid Beverage developed by CapitalBio eHealth Ltd. was recommended emphatically at the meeting, which, as stated by the research staffs, can be used to regulate and improve different disorders of intestinal flora.

Traditional Chinese medicine is the main form of treating diseases and building body in traditional Chinese medical science, and also an important resource for the development of foods and health care products, being known as "the homology of medicine and food". Many Chinese traditional medicines are both medicines and foods themselves, which can be used for both medicines and foods. The research on the regulation of intestinal flora by traditional Chinese medicines has just started. In 2016, studies have shown that polysaccharides in ginseng can enhance the growth rate of lactic acid bacteria and bacteroides, two main bacteria which metabolize ginsenosides, thereby increasing the absorption of ginsenosides and increasing the drug efficiency.

*Radix paeoniae alba* is one of 101 traditional Chinese medicines that can be used in health care products announced by the National Health and Family Planning Commission. Albiflorin is the main effective ingredient in *Radix paeoniae alba*. Modern pharmacological studies have shown that albiflorin has analgesic, sedative, anticonvulsant effects, and has effects on immune system, smooth muscles, and effects of liver protection. It is mainly used clinically for anti-epilepsy, sedation, anti-vertigo and treatment of geriatrics. The function of albiflorin in rapidly regulating and improving the balance of intestinal flora and the use thereof have not been disclosed so far.

Contents of the Invention

Regarding the deficiencies present in the prior art, an object of the invention is to provide new use of albiflorin as a new product for improving the function of intestinal flora system, which can significantly regulate the balance of intestinal flora, increase the amount of intestinal probiotics, particularly lactic acid bacteria, and thus can be used for preventing and/or treating a sub-health status and/or a disease caused by intestinal flora disturbance.

The research conducted by the invention has showed that albiflorin improves the function of intestinal flora system by regulating endogenous cannabinoid system, which has a close relationship with intestinal flora and irritable bowel syndrome (IBS), depression, anxiety.

The studies have shown that, cannabinoid receptor CB2 agonists can reduce intestinal inflammation and can reduce the incidence of cancer or inhibit the growth of cancer by inhibiting inflammatory responses, because inflammatory bowel disease (IBD) has an inseparable link with cancers ("Cannabinoid receptor 2 and several digestive diseases", January, 2016, World Chinese Journal of Digestology).

The research conducted by the invention has showed that albiflorin is a cannabinoid receptor CB2 agonist, which can up-regulate the expression of cannabinoid receptor CB2 in intestinal epithelial cells by increasing intestinal lactic acid bacteria, increase the pain threshold of intestine, relieve IBS, treat inflammatory bowel disease (IBD), and prevent and treat colon cancer.

The invention further provides a method of improving the function of intestinal flora system in an organism.

According to the invention, as a product for improving the function of intestinal flora system, albiflorin can be used for preparing a medicament, a food, a health care product, a food additive or a nutritional regulator for preventing and/or treating a sub-health status and a disease caused by intestinal flora disturbance. The sub-health status caused by intestinal flora disturbance is selected from intestinal system dysfunction and/or affective disorder; the disease is selected from one or more of irritable bowel syndrome, depression, anxiety, colitis and colon cancer.

Albiflorin is a monoterpenoid compound having a molecular formula of $C_{23}H_{28}O_{11}$, a molecular weight of 480.46, and a molecular structure as shown in the following formula. It is a natural active substance derived from roots of Paeonia lactiflora Pall or Paeonia veitchii Lynch, roots of P. suffrsticosa Andrz.

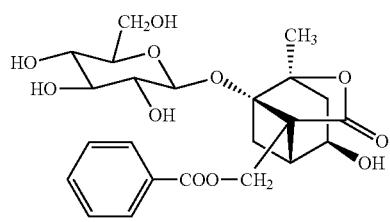

Formula (I)

According to the use provided by the invention, the pharmaceutically acceptable salt of the compound of Formula (I) may be one or more salts selected from the group consisting of citrate, hydrochloride, sulfate, malate, tartrate, citrate and phosphate.

In accordance with the disclosure of the invention, albiflorin or a pharmaceutically acceptable salt thereof, or an extract comprising albiflorin or a pharmaceutically acceptable salt thereof can be used for the preparation of a product for improving the function of intestinal flora system; albiflorin or a pharmaceutically acceptable salt thereof, or an extract comprising albiflorin or a pharmaceutically acceptable salt thereof can rapidly ameliorate and adjust intestinal flora disturbance, and improve and treat a sub-health status and a disease caused by intestinal flora disturbance by increasing intestinal metabolites, such as cholic acid, amino acids, vitamins and probiotic firmicutes in the intestinal tract of the tested rats, especially the amount of various lactic acid bacteria in the intestine, wherein the sub-health status is selected from intestinal system dysfunction and/or affective disorder; and the disease is selected from one or more of irritable bowel syndrome, depression, anxiety, colitis, and colon cancer.

In one aspect, the invention provides use of albiflorin or a pharmaceutically acceptable salt thereof, or an extract comprising albiflorin or a pharmaceutically acceptable salt thereof, in the preparation a product for improving the function of intestinal flora system.

Preferably, the product that improves the function of intestinal flora system is provided in the form of a medicament, a food, a health care product, a food additive or a nutritional regulator.

Preferably, improving the function of intestinal flora system is to prevent and/or treat a sub-health status and/or a disease caused by intestinal flora disturbance, particularly a significant decrease in the amount of intestinal probiotics and lactic acid bacteria;

Preferably, the sub-health status is selected from, but not limited to, intestinal system dysfunction and/or affective disorder; more preferably, the sub-health status is selected from intestinal system dysfunction and/or affective disorder caused by a decrease in the amount of intestinal probiotics, preferably lactic acid bacteria;

Preferably, the disease is selected from, but not limited to, one or more of irritable bowel syndrome, depression, anxiety, colitis, and colon cancer.

In another aspect, the invention provides a method for improving the function of intestinal flora system, comprising administering to a subject an effective amount of albiflorin or a pharmaceutically acceptable salt thereof, or an extract comprising albiflorin or a pharmaceutically acceptable salt thereof;

Preferably, improving the function of intestinal flora system is to ameliorate intestinal flora disturbance and increase the amount of intestinal probiotics, particularly lactic acid bacteria.

Preferably, improving the function of intestinal flora system is to prevent and/or treat a sub-health status and/or a disease caused by intestinal flora disturbance, particularly a significant decrease in the amount of intestinal probiotics and lactic acid bacteria;

Preferably, the sub-health status is selected from, but not limited to, intestinal system dysfunction and/or affective disorder; more preferably, the sub-health status is selected from intestinal system dysfunction and/or affective disorder caused by a decrease in the amount of intestinal probiotic, preferably lactic acid bacteria;

Preferably, the disease is selected from, but not limited to, one or more of irritable bowel syndrome, depression, anxiety, colitis and colon cancer.

In a further aspect, the invention provides a composition for improving the function of intestinal flora system comprising albiflorin or a pharmaceutically acceptable salt thereof, or an extract comprising albiflorin or a pharmaceutically acceptable salt;

Preferably, improving the function of intestinal flora system is to ameliorate intestinal flora disturbance and increase the amount of intestinal probiotics, particularly lactic acid bacteria.

Preferably, the composition for improving the function of intestinal flora system is a medicament, a food, a health care product, a food additive or a nutritional regulator.

Preferably, improving the function of intestinal flora system is to prevent and/or treat a sub-health status and/or a disease caused by intestinal flora disturbance, particularly a significant decrease in the amount of intestinal probiotics and lactic acid bacteria;

Preferably, the sub-health status is selected from, but not limited to, intestinal system dysfunction and/or affective disorder; more preferably, the sub-health status is selected from intestinal system dysfunction and/or affective disorder caused by a decrease in the amount of intestinal probiotics, preferably lactic acid bacteria;

Preferably, the disease is selected from, but not limited to, one or more of irritable bowel syndrome, depression, anxiety, colitis and colon cancer.

In a still further aspect, the invention further provides albiflorin or a pharmaceutically acceptable salt thereof, or an extract comprising albiflorin or a pharmaceutically acceptable salt thereof for improving the function of intestinal flora system;

Preferably, improving the function of intestinal flora system is to improve intestinal flora disturbance and increase the amount of intestinal probiotics, particularly lactic acid bacteria.

Preferably, improving the function of intestinal flora system is to prevent and/or treat a sub-health status and/or a disease caused by intestinal flora disturbance, particularly a significant decrease in the amount of intestinal probiotics and lactic acid bacteria;

Preferably, the sub-health status is selected from, but not limited to, intestinal system dysfunction and/or affective disorder; more preferably, the sub-health status is selected from intestinal system dysfunction and/or affective disorder caused by a decrease in the amount of intestinal probiotics, preferably lactic acid bacteria;

Preferably, the disease is selected from, but not limited to, one or more of irritable bowel syndrome, depression, anxiety, colitis and colon cancer.

The invention rapidly regulates and ameliorates human intestinal flora disturbance at multiple targets and increases the amount of intestinal probiotics, especially lactic acid bacteria by administering to a subject an effective amount of albiflorin or a pharmaceutically acceptable salt thereof, or an extract comprising albiflorin or a pharmaceutically acceptable salt thereof. It is used to prevent and treat a human sub-health status and disease caused by intestinal flora disturbance, especially a significant decrease in the amount of intestinal probiotics and lactic acid bacteria.

Compared with the prior art, the invention has the following advantages:

1. The invention restores and improves the function of intestinal system by increasing the amount of intestinal flora metabolites, such as cholic acid, vitamins and amino acids. The experiments demonstrated that albiflorin can quickly restore and ameliorate intestinal flora disturbance caused by various stress within one week after administration.

2. The invention improves the function of intestinal flora by promoting the growth of endogenous probiotics, especially by increasing the growth of lactic acid bacteria in a human body. In comparison with supplementing exogenous lactic acid bacteria in the prior art, such direct promotion of the growth of endogenous probiotics is much better in maintaining the activity, stability and abundance of lactic acid bacteria. Especially, the types of lactic acid bacteria supplemented by functional foods and beverages of exogenous lactic acid bacteria are limited, while the invention increases various intestinal lactic acid bacteria, and restores and enhances the overall function of intestinal lactic acid bacteria flora.

3. The first-line antidepressant SSRIs such as fluoxetine deviated the metabolism of intestinal flora in rats more from the normal states after administration, while the metabolism of intestinal flora in rats moved toward that of the normal group after administration of albiflorin, and almost completely overlapped with the normal group, indicating that albiflorin contributes to restoring the metabolism of intestinal flora of stressed rats to normal. Therefore, albiflorin not only has no the intestinal adverse reactions commonly seen for fluoxetine, but also can rapidly restore the balance of intestinal flora.

BRIEF DESCRIPTION OF THE DRAWINGS

The drawings are intended to illustrate that albiflorin has function of rapidly improving and regulating intestinal flora as shown by an integration of new generation of metabolomics and a high-throughput metagenomic sequencing.

BEST MODE OF CARRYING OUT THE INVENTION

The invention will be further explained below in conjunction with the specific examples. However, the following examples are only intended to illustrate the invention and are not intended to limit the scope of the invention.

In our previous research, it was found by an integration of new generation of metabolomics and a high-throughput sequencing technology that albiflorin can rapidly ameliorate the intestinal flora disturbance and restore the normal function of intestinal flora in rats.

Figure 1:
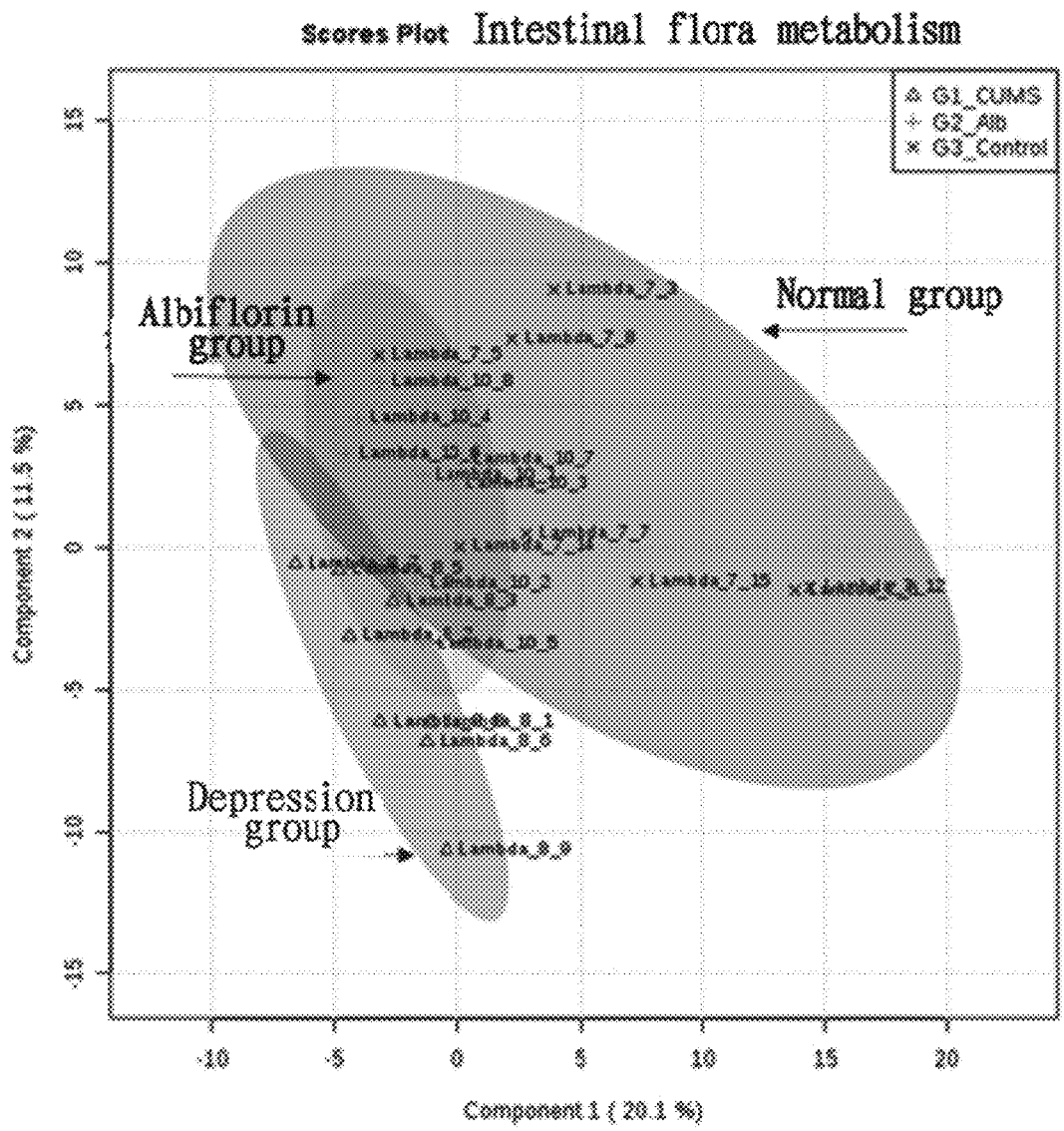
FIG. 1 is a multiple comparative analysis for targeted metabolomics (PLS-DA).

Example 1: The "Sub-Health" Status Stressed by Internal and External Environments Leads to Disturbance of Intestinal Flora We established a chronic unpredictable mild stress (CUMS) model of rats, and used a new generation of targeted metabolomics method to study the metabolic function of intestinal flora in stressed rats. A PLS-DA multivariable analysis showed that there was a significant difference in the intestinal flora metabolism of rats between the depression model group (depression group) and the blank group, as seen in FIG. 1.

Figure 2:
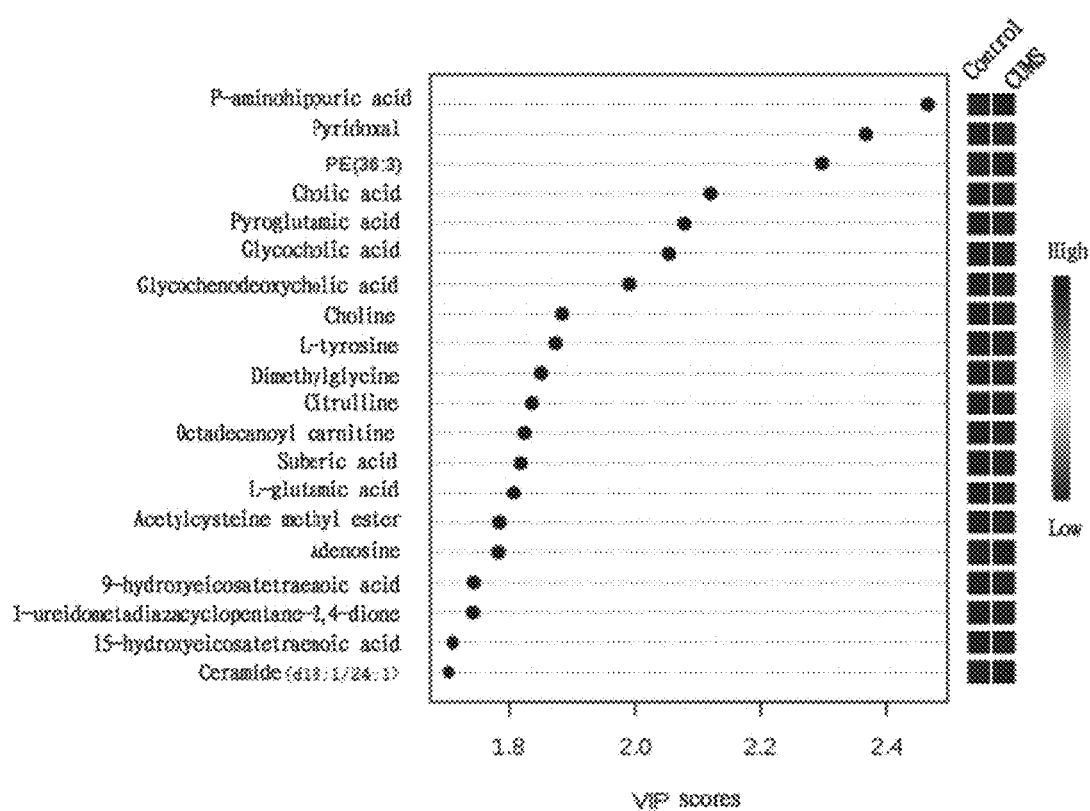
FIG. 2 is a VIP analysis of intestinal flora metabolism in the depression model group of rats and the blank group of rats (Top 20 metabolites, VIP>1.5 represents a significant difference).

It was shown by VIP analysis that the intestinal flora metabolism of the depression group was significantly lower than that of the blank group. Of the significant Top 20 metabolites in the two groups, 16 (80%) metabolites were significantly reduced in the depression model (VIP>1.5), as seen in FIG. 2. The reduced metabolites were mainly amino acids and vitamins and their derivatives, as seen in FIG. 2.

Figure 3:
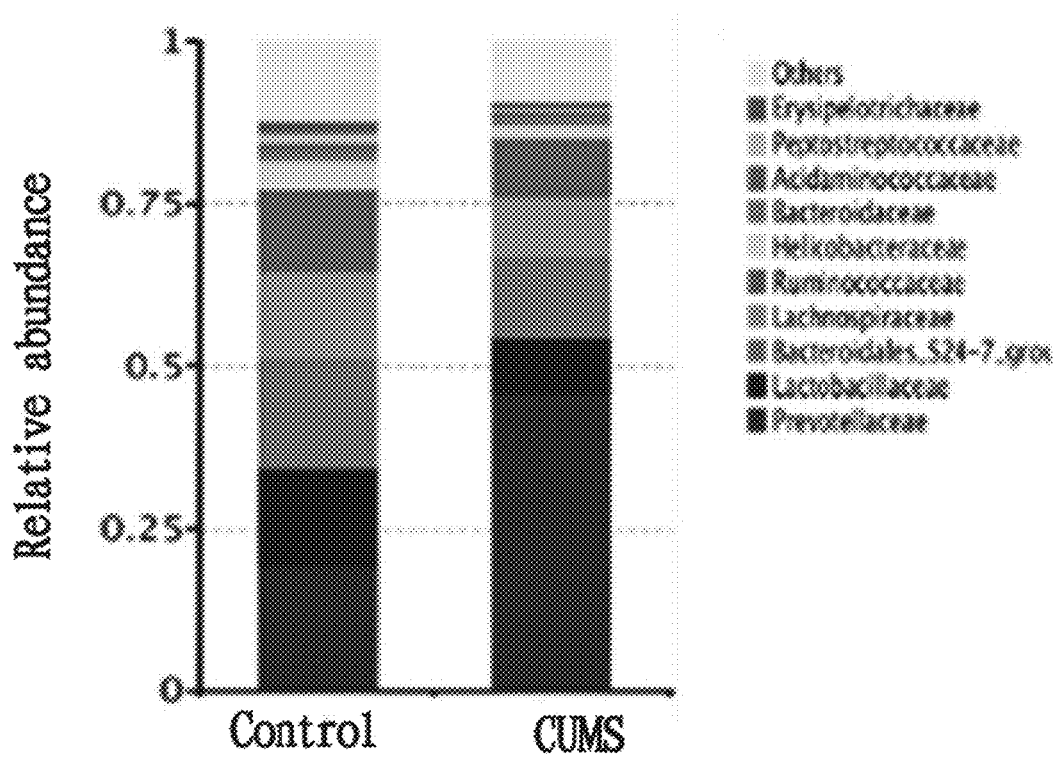
FIG. 3 is a composition analysis of intestinal flora in the model group of stressed rats (depression group) and the blank group of rats through a high-throughput sequencing. Control: the blank group; GUMS: the stressed rat model.

A high-throughput 16sRNA sequencing showed that there were significant changes in the composition and types of intestinal flora in the stressed rat model in comparison with the blank group, as seen in FIG. 3.

The studies have shown that the composition and dysfunction of intestinal flora were closely related to the stimulation from internal and external environments.

Example 2: 7 Days of Administration of Albiflorin can Quickly Restore the Composition and Function of Intestinal Flora in Stressed Rats We further administered the stressed model rats an albiflorin treatment for 7 consecutive days at each dose of 7 mg/k& for each treatment. 7 days later, we used metabolomics and a 16sDNA high-throughput metagenomic sequencing technology to re-evaluate the function and composition of intestinal flora in the rats. A multiple comparative analysis of metabolomics data (PLS-DA) showed that, after administration of albiflorin, the metabolism of intestinal flora of the rats moved toward that of the normal group, and almost completely overlapped with the normal group, indicating that albiflorin contributed to restoring the normal metabolism of intestinal flora in the stressed rats, as seen in FIG. 1. This was consistent with the results of analysis of flora composition.

Figure 4:
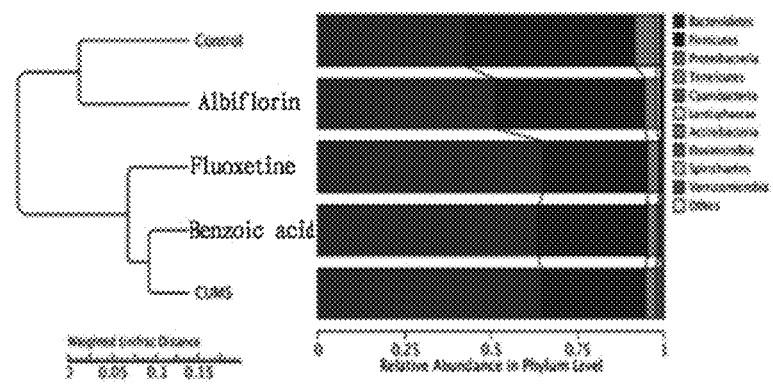
FIG. 4 is a cluster analysis of intestinal population composition after administration of albiflorin through a high-throughput metagenomic sequencing. Control: the blank group; Alb: the albiflorin group, CUMS: the rat model.

After 7 days of administration of albiflorin, a VIP analysis showed that the overall metabolism of intestinal flora was significantly improved compared with the depression group, as mainly shown by increased amounts of cholic acid, amino acids and vitamins, as shown in FIG. 4.

Figure 5:
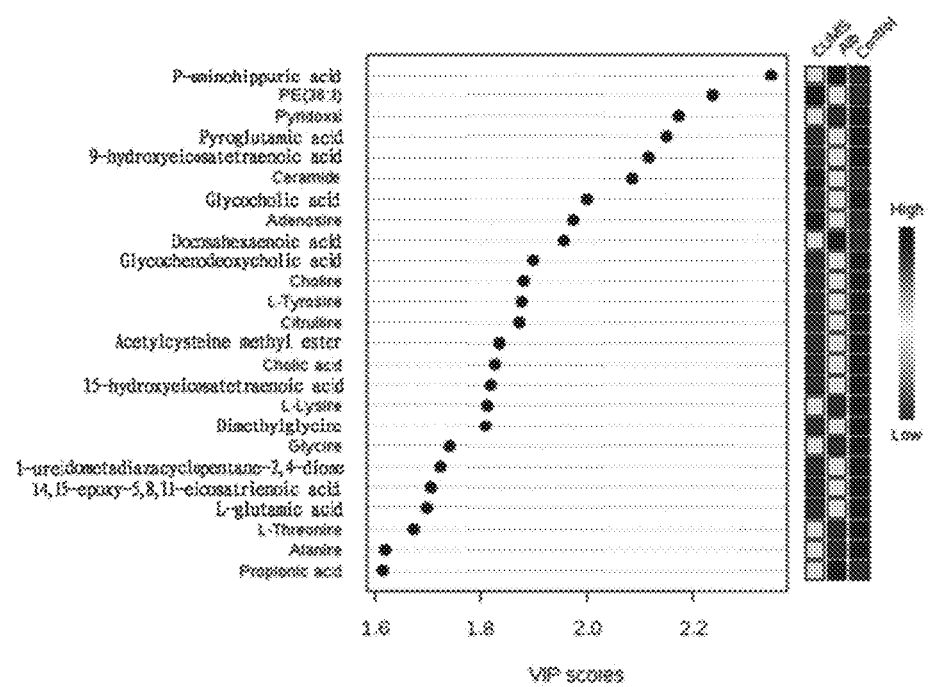
FIG. 5 shows that the metabolic disturbance of intestinal microorganisms of rats in the model group was corrected in the albiflorin group (Top 25 metabolites with significant changes after administration).

FIG. 5 is a graph showing the cluster analysis of intestinal flora composition correlation. The albiflorin administration group (Alb) was similar to the blank group (Control) in terms of composition, and was clustered together, showing no statistical difference ($P>0.05$) therebetween. Compared with the stressed rat model group, the amount of probiotic firmicutes, especially lactic acid bacteria was significantly increased.

Figure 6:
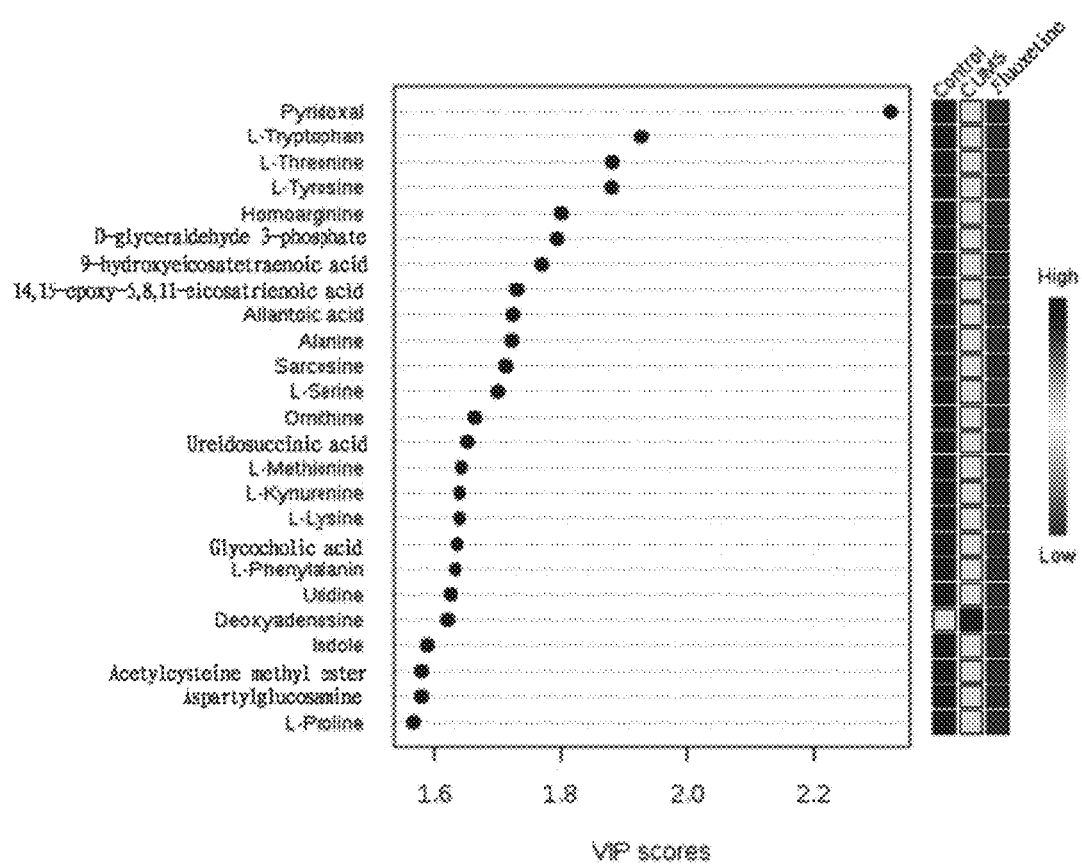
FIG. 6 is PLS-DA which showed that in the fluoxetine group the intestinal flora disturbance of rats was increased with respect to the model group.

Example 3: 7 Days of Administration of Fluoxetine Aggravated the Intestinal Flora Disturbance in Stressed Rats As a positive drug, fluoxetine was continuously administered for 7 days at each dose of 10 mg/kg/d. A multivariable PLS-DA analysis showed that the effect of fluoxetine was opposite to that of albiflorin, which deviated the metabolism of rat intestinal flora more from the normal state, as seen in FIG. 6.

In summary, an integrated study of metabolomics and a 16sRNA high-throughput sequencing showed that albiflorin has the function of rapidly regulating and improving intestinal flora. Albiflorin or an extract of *Radix paeoniae alba* or a functional composition containing albiflorin, can be used for preparing a food, a food additive, a health care product, or a medicament that can rapidly ameliorate intestinal flora disturbance, increase the amount of intestinal lactic acid bacteria, and these products have high application value and huge market potential.

The above description of the specific embodiments of the invention is not intended to limit the invention, and various modifications and changes can be made by those skilled in the art without departing from the spirit of the invention and shall fall within the scope as defined by the appended claims.

The invention claimed is:

1. A method for improving the function of an intestinal flora system, comprising administering to a subject an effective amount of albiflorin or a pharmaceutically acceptable salt thereof, or an extract comprising albiflorin or a pharmaceutically acceptable salt thereof, or administering to a subject a composition comprising albiflorin or a pharmaceutically acceptable salt thereof, or an extract comprising albiflorin or a pharmaceutically acceptable salt thereof;

wherein improving the function of the intestinal flora system comprises amelioration of an intestinal flora disturbance or an increase in the amount of an intestinal probiotic.

2. The method according to claim 1, wherein improving the function of the intestinal flora system is to treat a sub-health status and/or a disease caused by intestinal flora disturbance.

3. The method according to claim 1, wherein the intestinal probiotic is a lactic acid bacteria.

4. The method according to claim 2, wherein the disease caused by the intestinal flora disturbance is one or more of irritable bowel syndrome, depression, anxiety, colitis, or colon cancer.

5. The method according to claim 1, wherein the composition is a medicament, a food, a health care product, a food additive, or a nutritional regulator.

6. The method according to claim 2, wherein the sub-health status is an intestinal system dysfunction and/or an affective disorder.

7. The method according to claim 6, wherein the intestinal system dysfunction and/or an affective disorder is caused by a decrease in the amount of an intestinal probiotic.

8. The method according to claim 7, wherein the intestinal probiotic is a lactic acid bacteria.

* * * * *